United States Patent [19]

Frizziero

[11] Patent Number: 5,223,217
[45] Date of Patent: Jun. 29, 1993

[54] PROCESS AND DEVICE FOR THE STERILIZATION OF FILLING PLANTS

[75] Inventor: Denis Frizziero, Via della Repubblica, Italy

[73] Assignee: Capsulit S.p.A., Milan, Italy

[21] Appl. No.: 647,096

[22] Filed: Jan. 29, 1991

[30] Foreign Application Priority Data

Jan. 29, 1990 [IT] Italy .................. 19183 A/90

[51] Int. Cl.⁵ .................................................. A61L 2/06
[52] U.S. Cl. ........................................ 422/26; 422/31;
422/33; 422/108; 422/105; 422/292; 422/295;
141/1; 141/90; 141/91
[58] Field of Search ................. 141/1, 85, 90, 91;
422/26, 27, 28, 31, 33, 105, 108, 114, 116, 292,
295, 106; 222/148; 137/241

[56] References Cited

U.S. PATENT DOCUMENTS

| | | | |
|---|---|---|---|
| 3,650,678 | 3/1972 | Hansen | 137/241 |
| 4,353,398 | 10/1982 | Weiler et al. | 141/91 |
| 4,502,614 | 3/1985 | Weiler et al. | 222/148 |
| 4,601,885 | 7/1986 | McClure | 422/114 |
| 4,623,516 | 11/1986 | Weiler et al. | 422/28 |
| 4,804,114 | 2/1989 | Rizzardi et al. | 222/148 |
| 4,822,563 | 4/1989 | Joslyn | 422/31 |
| 4,989,649 | 2/1991 | Weiler et al. | 141/1 |
| 4,993,598 | 2/1991 | Groninger | 222/148 |

Primary Examiner—Robert J. Warden
Assistant Examiner—T. A. Trembley
Attorney, Agent, or Firm—Millen, White, Zelano & Branigan

[57] ABSTRACT

A method is provided wherein a plant for filling vials and similar containers comprising syringes and filling nozzles as well as nozzles for nitrogen injection is submitted to one or more washings and to a steam sterilization. Sterile nitrogen is then fed to the plant at slight overpressure to maintain the plant in sterile condition until it is used again. The device to carry out the method comprises a line for nitrogen injection, of the type normally used for nitrogen injection into vials, provided with an offtake connected by means of valves to the lines for water and steam feeding in order to alternatively feed water, steam or nitrogen to the syringes and filling nozzles, and steam or nitrogen to the injection nozzles and to the sterile filter for nitrogen filtration. The device is preferably automatically operated.

19 Claims, 1 Drawing Sheet

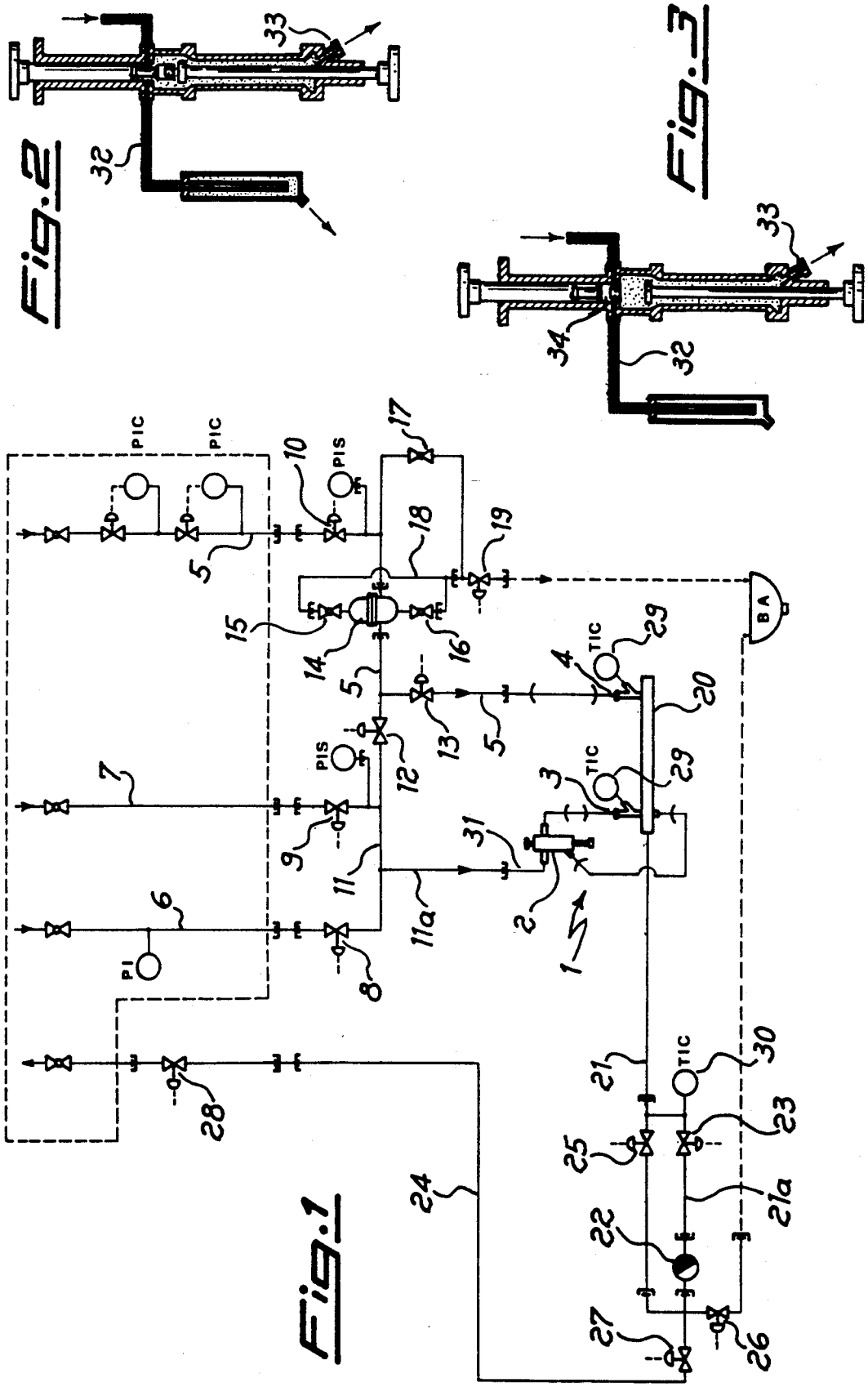

PROCESS AND DEVICE FOR THE STERILIZATION OF FILLING PLANTS

BACKGROUND OF THE INVENTION

1. Field of the Invention

The present invention concerns a process and a device for washing and sterilizing plants for filling vials and similar containers, and particularly plants for filling pharmaceutical vials.

2. Description of the Prior Art

Such plants essentially comprise, besides a (trailer-mounted or fixed) container for the liquid to be metered, a pumping system consisting of one or more syringes, one or more corresponding filling nozzles to fill the vials, and one or more nozzles to inject nitrogen into each vial before its filling with the product in order to avoid oxidation of the product.

Chiefly in the case of plants handling medicinal products, it is necessary to perform washing and sterilization of the plant before each operation cycle, namely when the type of product treated is changed, or, for example, at the beginning of the day, when the filling plant, off since the previous evening, is started again.

In any case, sterilization must be performed immediately before the plant use, because, if time passes between sterilization and use, the plant can be contaminated again. Furthermore, it is current practice to perform a washing operation at the end of the operating cycle in order to avoid the products remaining in the plant from crystallizing or hardening, thereby clogging the plant in some points; the operations of cleaning-sterilization are thus doubled.

It is obvious that this represents a considerable disadvantage in that the number of working hours of the plant during the day is reduced by the time necessary for its sterilization.

OBJECTS OF THE INVENTION

There is therefore the need to perform sterilization of the plant out of the time periods in which it is used for filling vials, though maintaining the plant sterile until its subsequent use.

SUMMARY OF THE INVENTION

An object of the present invention is to solve the aforementioned problems by providing a method and a device for sterilizing the filling plant at the end of its operating cycle and keeping it sterile until its subsequent use.

In particular, the invention relates to a process for the sterilization of a plant for filling vials and similar containers, of the type comprising one or more washing steps and one or more steps of steam sterilization, characterized by the step of injecting sterile gas into the plant at the end of the sterilization stage and maintaining the plant in an overpressure condition by means of the sterile gas until its subsequent use.

Furthermore, the invention relates to a device for the sterilization of a plant for vials and similar containers, the device being of the type comprising means to alternatively feed water or steam to the plant, characterized in that it comprises means to feed a sterile gas to the plant after its sterilization and to put and maintain the plant in overpressure condition by means of the gas until its subsequent use.

BRIEF DESCRIPTION OF THE DRAWINGS

The invention will be now further described with reference to the accompanying drawings, wherein:

FIG. 1 is a scheme of a device according to the present invention; and

FIGS. 2 and 3 are partial cross-sectional views of the syringes of the plant in two different positions during their sterilization.

DESCRIPTION OF THE PREFERRED EMBODIMENTS

According to the principle of the invention, the plant is submitted to the normal steps of washing and sterilization (and possibly to various washings and sterilizations) in a known way. At the end of the sterilization step, before steam pressure inside the plant falls to a value equal to the one atmosphere, the plant is fed with sterile gas and then put under light overpressure by means of the gas and maintained in overpressure condition until its subsequent use.

This allows performing plant sterilization at the end of the plant's operative cycle, for instance, at the end of a working day, when the plant has been stopped, in a way to have it ready for use the day after. Moreover, the time saving thus obtained can be advantageously maximized by performing the different steps in an automatic way.

FIG. 1 shows a scheme of a preferential embodiment of a device to perform the steps of washing/sterilization and inert gas introduction according to the afore described process. The device according to the invention comprises, besides the usual lines 6 and 7 for water and stem feeding to the plant, such as for instance sterile air, along nitrogen feed line 5.

The plant of FIG. 1 comprises a filling plant 1 consisting of a syringe 2 and a filling nozzle 3 connected thereto, and of a nozzle 4 for the injection of nitrogen (or similar substantially inert gas such as air) connected to the nitrogen feeding line 5. For greater simplicity, only one syringe with relevant filling and injection nozzles is illustrated, despite such plants usually foresee more than one; furthermore, all those parts of the filling plant which need no sterilization are not illustrated.

It is here pointed out that the word filling nozzle as used herein means the nozzle which serves to fill the vial with the product, while the term injection nozzle means the nozzle which serves to blow in nitrogen into the vial before its filling in order to avoid oxidation of the product.

The lines 5, 6 and 7 are each provided with valve means, 10, 8 and 9 respectively, to regulate the flow of the relevant fluids therein during the different steps of the process. Downstream of these valves, the lines 5, 6 and 7 are connected to each other by a common duct 11 from which line 11a branches off for feeding the syringe 2 and the nozzle 3 connected thereto. The syringe 2 is connected in a reversible way to the line 11a by means of a junction 31.

The duct 11 presents, along its portion between the lines 5 and 7, a valve 12 to regulate the passage of the fluids to and from the line 5. On the line 5, downstream of the junction with the common duct 11, there is provided a second valve 13 controlling the passage of the fluids to the nozzle 4. Still on the line 5, upstream of said junction, there is provided a sterile filter 14 of the "PALL" type, to filter nitrogen coming along the line 5 and guarantee its sterility.

As it can be noticed from the scheme of FIG. 1, the filter 14 can therefore receive steam too, or water, from the duct 11, whether the valve 12 is switched off or on. The process according to the invention only foresees steam injection to sterilize the filter together with the plant 1 and the remaining circuit of the device. The filter 14 is provided with outlets equipped with a manual discharge valves 15, and with a valve 16 for releasing condensate from the filter, the valves being connected to each other by a duct 18.

There is also provided a line for steam outlet from the filter 14, which is equipped with a manual valve 17 and is connected with the line 5 in a position between the filter and the valve 10, and with the duct 18 downstream of the manual valve or throttler 16. Downstream of this latter, along the line 18 there is a valve 19 to control the passage of fluids (steam and condensate) towards the drain discharge BA.

As mentioned above, valves 15, 16 and 17 are a kind of throttlers to be manually adjusted in an appropriate position at the moment of the plant installation and to be left in such a position during the different stages of the process.

FIG. 1 shows the nozzles 3 and 4 already housed inside their relevant sheaths of the manifold 20, which is also directly connected to the syringe 2 by means of a flexible duct, as well as with a drain line 21, which is provided with means to throttle or stop the flow along the same. Although these means might be constituted by whatever type of throttling, they preferably comprise a condenser 22, mounted with a valve 23, on an offtake 21a of the drain line 21. The offtake connects itself again with the drain line 21 of a point from which a recovery line for condensates 24 comes out.

In order to control the passage of fluids along the lines mentioned valve 23 and condenser 22, a first valve 25 mounted on the line 21 between two junctions with the offtake 21a, a second valve 26 also mounted on the line 21 and placed downstream of the offtake for the recovery of condensates, and a third valve 27 to regulate the passage of condensate to the line 24. Preferably, on the line 24 there is a further valve 28 to control the condensate flow back.

In correspondence with the housings of nozzles 3 and 4 in a manifold 20 there are provided means 29 to detect the temperature at the nozzles during the sterilization step. Similar means 30 are provided on the offtake 21a to control, as a function of temperature and by way of valves 23 and 25, the passage from the direct drain line 21 to the condenser 22.

The detectors 29, 30 are connected to a temperature recorder of known type (for example, a recorder of CHESSEL type) which is in turn connected to a control console, of known type as well, such as for instance the one called SIMATIC 55 of Siemens, and inserted in the general control board of the machine. Recorder and console are not shown in FIG. 1.

Detectors 29 are preferably set at 121° C. and detector 30 is set at 40° C.

For better operating safety, mainly in case of automatic operation, a plurality of sensors are also envisaged to control the correct execution of each stage, and more in particular sensors for the nozzles positioning, namely sensors for checking the actual connection of the plant circuit to the lines for water, steam and inert gas feeding, sensors checking the actual insertion of the nozzles into their relevant housings of the manifold 20; sensors of correct positioning of the syringe plunger in the washing/sterilization position, and sensors for checking the condensate level in said condenser 22, to detect presence of excessive condensate due for example to the partial relaxation of a flexible tube and the subsequent formation of much more condensate than it normally occurs.

There are also pressure switches, one for each feeding line 5, 6, 7, to check the actual feeding of water, steam and nitrogen along these lines.

The pressure switches, too, are connected to the console to generate an alarm signal in case feeding stops.

All these are sensors of known type and commercially available and are connected in a known way to the control console to generate an alarm signal and stop the machine cycle in case preset operating conditions are not met.

As already previously mentioned, the afore described device allows to carry-out the process according to the invention in an automatic way, by control from the console which controls a panel of solenoids controlling in turn a circuit for operating the valves which are preferably pneumatic valves.

To carry-out the process, at the end of the operations of the vials filling, first of all the nozzles 3 and 4 are positioned into their relevant housings of manifold 20 and the junction 31 is displaced from the trailer-mounted container of the product connecting it to the line 11a. Then the syringes are brought in washing/sterilization position (as shown in FIG. 2 and as known in the technique) to be emptied from the remaining product.

At this point all valves are closed except the throttlers 15, 16 and 17 which, as already said, are adjusted at the moment of the plant installation and are no more modified. Then a first "dynamic" washing of the syringe and the nozzle 3 is performed by opening only the valves for water feeding, 8, and direct drainage, 25 and 26. In this type of washing, the syringe operates by sucking water and conveying it to the nozzle 3.

At the end of this washing, whose duration is set on the control board in a known way, the water flow is stopped by closing the valve 8 and the syringe is brought to the position of washing/sterilization shown in FIG. 2.

Afterwards a second washing of the "static" type is carried out with the valves under similar conditions as for the preceding dynamic washing, for a further period of time which, too, can be set in a known way (e.g., by means of a keyboard unit OP 393 by Siemens)on the control board.

At the end of this washing, according to a preferred embodiment of the invention, the valve 8 is closed and the valves 12 and 10 are opened to inject nitrogen into the lines and discharge water from them and from the nozzle 3. The predetermined and set time for this operation is generally very restricted, of the order of approximately 1 minute, at the end of which the valve 10 is closed again while valves 12, 25 and 26 remain open.

In the subsequent step of sterilization, the condensate flow back valve 28, steam feeding valve 9, steam exhaust valve 19 from the sterile filter 14 and valve 13 allowing passage to the nozzle 4 are opened.

Steam thus begins to circulate along all the lines and the filter 14, until it escapes from the exhaust line 21 and the valve 19.

Once the previously set temperature is reached (generally 40° C.) and detected by the detecting means 30 placed on the line 21, the drainage valves 25 and 26 are automatically closed and simultaneously the valve 23 for the condenser 22 operation and the condensate recovery valve 27 are opened, thus connecting the line 21 to the condensate recovery line 24 through the condenser 22. As previously mentioned, the function of the condenser 22 is mainly that of throttling the line 21a, limiting the steam flow therethrough and so keeping the lines of the device and the plant under pressure.

In this way it is possible to bring said lines at the preferred sterilization temperature, which is generally at least 121° C. More in particular, when this temperature is detected by sensors 29, the temperature recorder actuates through the console the start up of the period of sterilization at 121° C., which period generally lasts approximately 0.5 hours.

Sensors 29 also check that during this period of sterilization no significant drops in temperature occur at the nozzles 3 and 4. In this way sterility of the plant and of the device lines is ensured.

Furthermore, in this step, the filter 14 as well is sterilized.

Once the preset period of time is over, the valve 9 of steam inlet is closed.

The last step of inert gas introduction maintenance of the sterile conditions of the circuit begins when the pressure of steam remaining in the device lines has decreased to sufficiently low values to allow nitrogen injection at slight overpressure, in any case at a pressure higher than the atmospheric one to avoid the circuit from being contaminated again by the external environment.

At this point, all the valves are closed except the valve 12 and the valve 10 of nitrogen inlet.

The duration of this stage depends on the time that intervenes between sterilization and the subsequent use of the filling plant, and it is manually terminated at the moment of plant re-use.

According to a different embodiment of the process, the sterilization step is subdivided into two parts, lasting approximately 0.5 hours each. In the first part, sterilization is carried out as previously described. In the second part the valve 34 of the syringe is moved upwards to the position shown in FIG. 3: in this position the valve cuts off the steam flow towards the side outlet 32 and the relevant filling nozzle, conveying all steam towards to the other outlet 33 and thus improving the sterilization of the lower section of the syringe.

As previously mentioned, the correct execution of the different stages of the process is controlled by different types of sensors which, in case of failure or troubles, generate a signal activating an alarm and simultaneously stopping the device operation. This is particularly useful in case of automatic operation controlled by the console included in the machine control board. In case of troubles and alarm, the operator will manually restore the plant operation after having eliminated the causes of the trouble.

Moreover, it is here pointed out that, despite the invention has been described with particular reference to a filling plant of the type using a trailer-mounted product container, a similar device and similar procedure can be used in case of a fixed container. In this case the product tank will be equipped with exhaust means for the condensate similar to those described with reference to the sterile filter 14, and the line 11a will be connected to the product tank.

Similarly the device and the process according to the invention can be applied to a plant not provided with nozzles for nitrogen injection during vials filling. In this case the only difference consists in the absence of the nozzle 4 and of that section of line 5 which leads from the common duct 11 to nozzle 4. Also the valve 13 and the temperature sensor 29 related to the nozzle for nitrogen injection will obviously be absent.

I claim:

1. A process for the sterilization of a filling plant comprising at least one pumping means and at least one filling nozzle associated therewith, for filling containers with a product, said process comprising:

subjecting a filling plant to a washing step wherein water from a water supply line is conducted through at least one pumping means of said filling plant and at least one filling nozzle of said filling plant;

subjecting said filling plant to a sterilization phase wherein sterilizing steam is conducted through said at least one pumping means and at least one filling nozzle; and introducing a sterile gas into said filling plant via a sterile gas supply line having a sterile filter and maintaining said at least one pumping means and at least one filling nozzle in a pressurized condition until said filling plant is subsequently used again for filling containers;

said water supply line, steam supply line and sterile bas supply line being in fluid communication with a common duct, said common duct having a branched line in fluid communication with said at least one pumping means whereby water, sterilizing steam and sterile gas can be delivered to said at least one pumping means and at least one filling nozzle via said branched line;

wherein, before said washing step, said filling plant is connected to said branched line and said at least one filling nozzle is positioned in a housing means within a manifold, said manifold having means for detecting the temperature of said at least one filling nozzle during sterilization and a drain line, said drain line having means for detecting the temperature of fluids therein;

said washing step being performed by opening only valves for delivering water from said water supply line and discharging liquid from said manifold via said drain line;

said washing step being terminated and said sterilization phase begun by terminating delivery of water and beginning delivery of steam to said at least one pumping means, filling nozzle, and sterile filter;

during said sterilization phase throttling means positioned within said drain line of said manifold is actuated when a preset temperature of fluids within said drain line is reached and thereafter said at least one pumping means, said at least one filling nozzle, and said sterile filter are maintained at a preset sterilization temperature by feeding stem until said sterilization phase is over; and after termination of said sterilization phase, introduction of sterile gas is begun by feeding sterile gas to said filling plant and closing discharge valves positioned in said drain line, thereby pressurizing said filling plant, said filling plant being maintained in said pressurized condition by said sterile gas until subsequent use thereof.

2. A process according to claim 1, further comprising detecting and controlling execution of each step by:
   sensors for detecting connection to said water supply line, steam supply line, and sterile gas supply line;
   a sensor for detecting the position of a plunger within said at least one pumping means;
   a sensor for detecting insertion of said at least one filling nozzle in said housing means;
   pressure sensors for detecting feeding of water, steam and sterile gas along their relevant supply lines; and
   a sensor for detecting condensate level inside said throttling means of said drain line, wherein said throttling means is a condenser.

3. A process according to claim 1, further comprising eliminating washing water from said at least one pumping means and at least one filling nozzle and simultaneously injecting sterile gas into same.

4. A process according to claim 1, wherein said sterile gas is nitrogen.

5. A process according to claim 1, wherein said filling plant further comprises:
   at least one injection nozzle for injecting inert gas into a container, said at least one injection nozzle being in fluid communication with said sterile gas supply line at a point downstream of the connection between said common duct and said sterile gas supply line; and
   wherein said at least one injection nozzle is subjected to sterilizing steam simultaneously with said at least one pumping means, said at least one filling nozzle and said sterile filter.

6. An apparatus for sterilizing a filling plant comprising at least one pumping means and at least one filling nozzle associated therewith for filling containers with a product, said apparatus comprising:
   a sterile gas supply means having a gas supply source, a sterile gas conduit, a sterile filter, and a sterile gas regulating valve;
   a sterilizing steam supply means comprising a sterilizing steam supply source, a sterilizing steam conduit, and a steam regulating valve;
   a water supply means comprising a water supply source, a water supply conduit, and a water regulating valve;
   a common duct in fluid communication with each of said sterile gas supply means, sterilizing steam supply means and water supply means, said common duct having a valve means for interrupting fluid communication between said sterile gas conduit and both said sterilizing steam supply conduit and water supply conduit, said common duct further comprising a branched conduit for delivery of water, sterilizing steam or sterile gas to at least one filling nozzle of a filling plant via at least one pumping means of a filling plant;
   a manifold having means for housing at least one filling nozzle of a filling plant therein, said manifold also being connected with a drain line;
   throttling means, positioned in said drain line, for throttling steam flow;
   temperature detecting means associated with the means for housing at least one filling nozzle of a filling plant to detect the temperature thereof during sterilization; and
   means for controlling said steam regulating valve, water regulating valve, and sterile gas regulating valve.

7. An apparatus according to claim 6, wherein said throttling means consists of a condenser which can be alternatively connected, through a drain valve means, to said drain line or to a line for condensate recovery.

8. An apparatus according to claim 7, wherein said drain valve means comprises:
   a first valve and a second valve positioned on said drain line;
   a third valve associated with said condenser and positioned on one side thereof, both said condenser and said third valve means being positioned on an offtake of said drain line which is also connected to said line of condensate recovery, said offtake being connected to said drain line at a point on one side of said first valve and connected again to said drain line at a point on the other side of said first valve between said first valve and said second valve; and
   a fourth valve positioned on said line of condensate recovery.

9. An apparatus according to claim 8, further comprising a plurality of sensors comprising:
   sensors to detect connection of each of said sterilizing steam conduit, water supply conduit, and sterile gas conduit to said common duct;
   a sensor for detecting the position of a plunger within at least one pumping means of a filling plant;
   a sensor for detecting insertion of at least one filling nozzle of a filling plant within said means for housing of said manifold;
   a pressure switch on each of said sterilizing steam conduit, water supply conduit, and sterile gas conduit for detecting fluid flow within each of said conduits; and
   a sensor for detecting condensate level in said condenser.

10. An apparatus according to claim 7, further comprising a plurality of sensors comprising:
   sensors to detect connection of each of said sterilizing steam conduit, water supply conduit, and sterile gas conduit to said common duct;
   a sensor for detecting the position of a plunger within at least one pumping means of a filling plant;
   a sensor for detecting insertion of at least one filling nozzle of a filling plant within said means for housing of said manifold;
   a pressure switch on each of said sterilizing steam conduit, water supply conduit, and sterile gas conduit for detecting fluid flow within each of said conduits; and
   a sensor for detecting condensate level within said throttling means, wherein said throttling means is a condenser.

11. An apparatus according to claim 6, wherein said sterile filter is positioned between said gas supply source and the point at which said common duct is connected to said sterile gas conduit, and said valve means of said common duct controls fluid passage along said common duct to and from said sterile filter.

12. An apparatus according to claim 6, wherein said temperature detecting means and said another temperature detecting means are connected to means for processing signals coming therefrom and means for generating corresponding control signals to said steam regulating valve, water regulating valve and sterile gas regulating valve.

13. A device according to claim 12, wherein said regulating valves are pneumatic valves and the relevant control means comprise a panel of solenoids connected to said pneumatic valves.

14. An apparatus according to claim 6, wherein said sterile gas supply means further contains a steam outlet line with steam discharge valve means positioned between said sterile gas regulating valve and said sterile filter, whereby sterilizing steam introduced into said sterile filter via said common duct is discharged by said steam outlet line.

15. An apparatus according to claim 14, wherein said sterile filter further comprises a gas outlet line with valve means and a condensate drain line with valve means.

16. An apparatus according to claim 6, further comprising an inert gas injection conduit for introducing inert gas into a container in at least one injection nozzle of a filling plant, said inert gas injection conduit being in fluid communication with said sterile gas conduit at a point between said sterile filter and said valve means of said common duct; and
- said manifold further comprising means for housing at least one injection nozzle of a filling plant whereby sterilizing steam introduced into at least one injection nozzle of a filling plant via said common duct and sterile gas conduit is discharged from said manifold via said drain line.

17. An apparatus according to claim 6, further comprising another temperature detecting means positioned on said drain line to detect the temperature of fluids escaping via said drain line, and wherein said manifold further comprises means for directly connecting said manifold to at least one pumping means of a filling plant.

18. An apparatus for sterilizing a filling plant comprising at least one pumping means and at least one filling nozzle associated therewith, for filling containers with product, said apparatus comprising:
- a sterile gas supply means having a gas supply source, a sterile gas conduit, a sterile filter, and a sterile gas regulating control valve;
- a sterilizing steam supply means comprising a sterilizing steam supply source, a sterilizing steam conduit, and a steam regulating valve;
- a water supply means comprising a water supply source, a water supply conduit, and a water regulating valve;
- a common duct in fluid communication with each of said sterile gas supply means, sterilizing steam supply means and water supply means, said common conduit having a valve means for interrupting fluid communication between said sterile gas supply conduit and both said sterilizing steam supply conduit and water supply conduit, said common duct further comprising a branched conduit for delivery of water, sterilizing steam or sterile gas to at least one filling nozzle of a filling plant via at least one pumping means of a filling plant;
- a manifold means into which at least one filling nozzle of a filling plant can be inserted, said manifold means having a condensate discharge line for removal of fluid from said manifold; and
- condensate discharge control means comprising valve means for regulating condensate flow through said condensate line and condenser throttling means for throttling steam flow through said condensate line.

19. An apparatus for sterilizing a filling plant comprising at least one pumping means and at least one filling nozzle associated therewith for filling containers with a product, said apparatus comprising:
- a sterile gas supply means having a gas supply source, a sterile gas conduit, a sterile filter, and a sterile gas regulating valve;
- a sterilizing steam supply means comprising a sterilizing steam supply source, a sterilizing steam conduit, and a steam regulating valve;
- a water supply means comprising a water supply source, a water supply conduit, and a water regulating valve;
- a common duct in fluid communication with each of said sterile gas supply means, sterilizing steam supply means and water supply means, said common duct having a valve means for interrupting fluid communication between said sterile gas conduit and both said sterilizing steam supply conduit and water supply conduit, said common duct further comprising a branched conduit for delivery of water, sterilizing steam or sterile gas to at least one filling nozzle of a filling plant via at least one pumping means of a filling plant;
- an inert gas injection conduit for introducing inert gas into a container via at least one injection nozzle of a filling plant, said inert gas injection conduit being in fluid communication with said sterile gas conduit at a point between said sterile filter and said valve means of said common duct; and
- a manifold having means for housing at least one filling nozzle of a filling plant, said manifold also being connected with a drain line, said manifold further having means for housing at least one injection nozzle of a filling plant whereby sterilizing steam introduced into at least one injection nozzle of a filling plant via said common duct and sterile gas conduit is discharged from said manifold via said drain line.

* * * * *